(12) United States Patent
Watts et al.

(10) Patent No.: US 8,128,611 B2
(45) Date of Patent: Mar. 6, 2012

(54) PRE-ASSEMBLED MEDICAL FLUID FLOW SYSTEM AND METHOD OF MAKING SAME

(75) Inventors: Walter Timothy Watts, Arlington Heights, IL (US); Kyungyoon Min, Kildeer, IL (US); Daniel Martin Karlovsky, Cary, IL (US)

(73) Assignee: Fenwal, Inc., Lake Zurich, IL (US)

( * ) Notice: Subject to any disclaimer, the term of this patent is extended or adjusted under 35 U.S.C. 154(b) by 438 days.

(21) Appl. No.: 12/327,072

(22) Filed: Dec. 3, 2008

(65) Prior Publication Data

US 2010/0137826 A1 Jun. 3, 2010

(51) Int. Cl.
*A61B 19/00* (2006.01)
(52) U.S. Cl. ........ 604/410; 604/6.16; 604/408; 604/406
(58) Field of Classification Search ................ 604/6.16, 604/403, 408, 410, 406
See application file for complete search history.

(56) References Cited

U.S. PATENT DOCUMENTS

| | | | |
|---|---|---|---|
| 4,157,723 A | | 6/1979 | Granzow et al. |
| 4,265,760 A | * | 5/1981 | Abel et al. ............. 210/282 |
| 4,332,122 A | * | 6/1982 | Williams .................. 53/425 |
| 4,978,446 A | * | 12/1990 | Lobdell ................ 210/206 |
| 5,009,654 A | | 4/1991 | Minshall et al. |
| 5,269,946 A | * | 12/1993 | Goldhaber et al. ........... 210/767 |
| 5,690,815 A | | 11/1997 | Krasnoff et al. |
| 6,322,488 B1 | | 11/2001 | Westberg et al. |
| 2003/0070969 A1 | * | 4/2003 | Muller et al. .................. 210/91 |
| 2004/0236263 A1 | | 11/2004 | Van Waeg et al. |
| 2006/0011545 A1 | | 1/2006 | Latza |
| 2008/0047898 A1 | | 2/2008 | Sommer |

FOREIGN PATENT DOCUMENTS

WO WO/2007/041716 A1 4/2007

OTHER PUBLICATIONS

Search Report of Application No. GB 0921276.2 dated Mar. 26, 2010.

* cited by examiner

*Primary Examiner* — Leslie Deak
(74) *Attorney, Agent, or Firm* — Cook Alex Ltd.

(57) ABSTRACT

A pre-assembled medical fluid flow system and method of making same are disclosed. The system includes a first sterilized fluid flow system component, a second sterilized fluid flow system component and a flow path for providing fluid communication therebetween. The flow path includes an isolated portion. An openable closure isolates the isolated portion from the first sterilized fluid system component, and a microorganism filter is disposed between and isolates the isolated portion of the flow path and the second sterilized fluid flow system component. Therefore, fluid from the isolated portion of the flow path must flow through the microorganism filter to reach the second sterilized fluid flow system component.

19 Claims, 2 Drawing Sheets

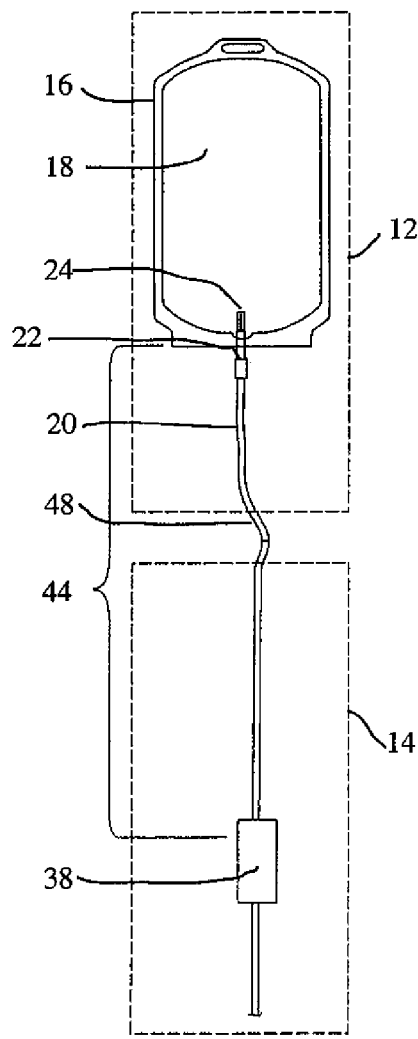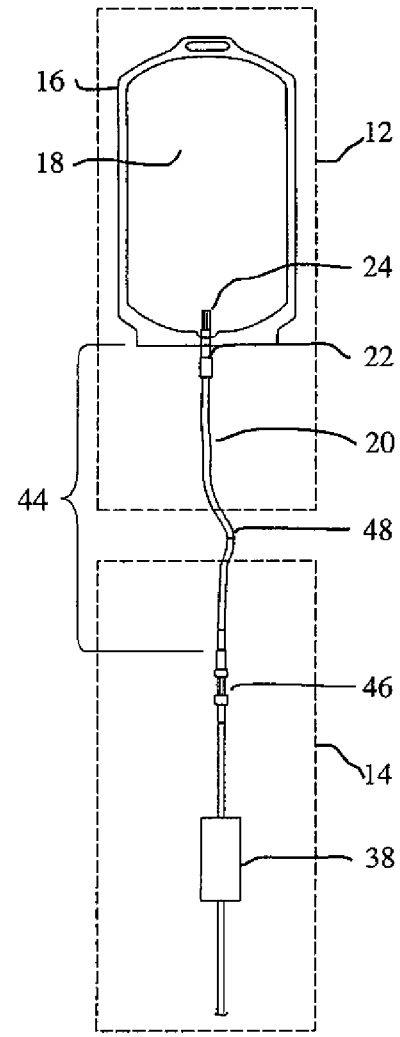

PRE-ASSEMBLED MEDICAL FLUID FLOW SYSTEM AND METHOD OF MAKING SAME

The present disclosure relates generally to medical fluid flow systems and to methods for sterilizing and assembling such systems. More particularly, the present subject matter relates to pre-assembled medical fluid flow systems and to methods for making such systems, and still more particularly to, but not exclusively, such pre-assembled systems in which it is preferred or required that at least one portion of the system be sterilized with a different sterilization technique than at least one other portion of the system.

Disposable medical fluid flow systems that, at least in part, are pre-sterilized and pre-assembled are used in a wide variety of medical applications, including without limitation administration of medical fluids to a patient for therapeutic and/or diagnostic purposes, blood and/or blood component or other cell collection or processing, dialysis and other procedures. Such flow systems commonly employ one or more pre-filled containers or other sources of medical fluid or agent and an associated fluid flow circuit or system (sometimes called a tubing set) containing the necessary flow tubing, valves, flow controllers, process chambers and the like to carry out the particular procedure, either alone or in cooperation with a reusable controller or other device. It is not unusual, for example, for a medical fluid flow system to include or be used in association with a container of a suitable drug, saline, anticoagulant, dextrose solution, sterile water, cell preservative or the like, as just a few examples.

Such fluid flow system can pose manufacturing difficulties. The pre-filled containers of medical liquid, powder or other agent that is administered to the patient or otherwise employed in the medical fluid flow system, often require different sterilization techniques than other portions of the fluid flow system. For example, plastic tubing, empty containers, flow control devices and/or processing devices or chambers, which do not contain any substantial amount of liquid or other agent, may be sterilized with gamma or electron beam (e-beam) radiation or by exposure to a sterilizing gas, e.g., ethylene oxide. However, gas sterilization would be ineffective to sterilize an agent, such as a liquid, powder or drug, contained in a sealed container, and exposing the agent to ionizing radiation may degrade or otherwise have a deleterious effect on the agent.

For this reason, a number of different approaches have been used in providing disposable medical fluid flow systems that employ pre-filled containers of medical fluid, drugs or other agents. For example, it is very common to provide sealed containers of an agent, such as saline, dextrose, drugs or other, entirely separate from the remainder of the fluid flow system assembly, leaving assembly the responsibility of the end user. In such an arrangement, the fluid flow system or assembly includes an access member, such as a piercing spike, for insertion into a port on the container. This, of course, requires the medical facility to separately order, track and stock the agent container and flow system. When it must be used, the medical professional must separately order or prescribe the different components and then assemble them for the procedure in question. These steps increase the administrative chores and costs, and separate ordering and assembly by the medical professional has attendant risks of errors. Further, joining the fluid flow system and container typically requires exposing both the access member and associated container port to non-sterile ambient environment, potentially increasing the risk of infection for the patient.

Other systems have provided the pre-filled container of agent pre-assembled (pre-attached) with at least part of the fluid flow system. This, however, has typically required added manufacturing steps and/or equipment, adding to product cost. For example, one concept for the manufacturer of such systems employs the use of a sterile docking device, such as a device disclosed in U.S. Pat. No. 4,157,723. As illustrated there, the sterile docking device comprises a pair of mating members, each having a facing membrane. One of the mating members is connected to a pre-sterilized container of liquid, drug or other agent and the other mating member is attached to a pre-sterilized fluid flow system, which may include one or more empty containers. After the two members are joined, the docking device is exposed to radiant energy, causing the membranes to melt and form a sterile fluid pathway through the device. Fluid may then be transferred from the initial container into an empty container in the fluid flow system, and the flow path sealed and severed. The initial container and sterile docking device is then discarded. While this works satisfactorily, it entails multiple manufacturing steps of transferring solution from one container to another in a sterile manner and the associated quality control procedures with such a step. It also requires the disposal of a portion of the product with increased product and waste cost.

One additional technique has been disclosed for pre-assembling disposable medical fluid flow systems which include one portion, such as a fluid filled container, which must be sterilized by one technique and another portion, such as empty tubing, flow control members, processing chambers and the like (the dry portion) which is preferably sterilized in other ways. This technique, as described in U.S. Pat. No. 5,009,645, employs requires a manufacturing procedure employing an electron beam or the like to sterilize isolated portions of the assembly after they have been joined together. After the isolated regions are joined and sterilized, the clamps or frangibles which isolate the regions may then be opened to allow for direct communication between the associated container of liquid or the like and the remainder of the fluid processing assembly. Such procedure and the use of e-beam or similar radiation, of course, requires a substantial investment in manufacturing equipment as well as additional procedures and safeguards during manufacture.

To avoid the use of more complicated manufacturing processes, it has also been disclosed to use sterilizing filters on the inlet flow line that couples a pre-sterilized liquid container or the like to a separately sterilized fluid flow tubing system. Such an arrangement is illustrated in U.S. Pat. No. 4,978,446. In that approach, however, the medical personnel are required to manually join the fluid flow tubing system to the fluid container, such as by spiking the fluid container with a piercing member associated with the fluid flow system. In addition to the administrative requirements for individually ordering, storing and prescribing solutions and disposable flow systems or sets, there is the added possibility of errors, such as by connection of a container of an incorrect liquid or other agent or an improper flow system to be used in association with the procedure.

The subject matter of the present application is addressed in one aspect to providing a pre-assembled, disposable medical fluid flow system, which has portions that are preferably or necessarily sterilized with different techniques or otherwise are separately manufactured, but which does not require separate spiking or accessing steps by the medical professional user and does not require the additional cost, equipment or steps of the electron beam radiation or sterile docking procedures described above.

SUMMARY

In accordance with one aspect, the present subject matter is directed to a pre-assembled, disposable medical fluid flow system and method for making it that includes portions which may be preferably or necessarily sterilized using different techniques or are separately manufactured for other reasons and does not require separate spiking or assembly by the medical professional, or the assembly steps and operation associated with the e-beam procedure or sterile connection procedures described above.

More specifically, in accordance with the present subject matter a pre-assembled disposable medical fluid flow system may be provided, which comprises at least one first sterilized fluid flow system component and at least one second sterilized fluid flow system component. A flow path is fixedly connected to the first and second sterilized fluid flow system components for providing fluid communication therebetween. The flow path includes an isolated portion, which may be a non-sterile portion, located between the first and second sterilized fluid flow system components. An openable closure isolates the first sterilized fluid flow system component from the isolated portion of the flow path to prevent any contamination of the first sterilized fluid flow system component if the isolated portion is not sterile, and a micro-organism filter is disposed between and isolates the isolated portion of the flow path and the second sterilized fluid flow system component, such that any fluid from the isolated portion of the flow path, which may be non-sterile, must flow through the micro-organism filter to reach the second sterilized fluid flow system component.

Such a medical fluid flow system may be manufactured without the more complicated and expensive procedures and equipment employed in the electron beam sterilization system, or in the sterile docking systems described above. More specifically, a method for making such a pre-assembled disposable medical fluid flow system in accordance with the present subject matter may include sterilizing a first fluid flow system component, and sterilizing a second fluid flow system component separately from the first component. These components may be sterilized separately because the sterilization techniques are completely incompatible or because different sterilization techniques or separate sterilization may be preferred from a manufacturing standpoint.

In accordance with one aspect of the present method, a fluid flow path is provided between the first and second fluid flow system components and fixedly attached thereto. The fluid flow path includes an isolated portion, which may not be sterile. The method includes isolating the first fluid flow system component from the isolated portion of fluid flow path with an openable closure and providing a micro-organism filter between the isolated portion of the flow path and the second fluid flow system component to isolate one from the other and filter any fluid passing from the isolated portion of the flow path to the second fluid flow system component.

When the above method is employed, the resulting medical fluid flow system is provided to the user, for example the medical professional, in a pre-assembled arrangement that allows for the flow of liquid or other agent, for example, from the first fluid flow system component into the second fluid flow system component in a manner that maintains the sterility of the liquid. For example, when the medical professional wishes to use such a pre-assembled disposable medical fluid flow system, the only required step is to open the openable closure, which would allow fluid to flow from the first fluid flow system component into the second fluid flow system component. Although the fluid flows through the isolated portion of the fluid flow path which may not be sterile, the fluid must subsequently pass through the micro-organism filter before before reaching the second fluid flow system component. The micro-organism filter blocks any bacteria and preferably any virus that may have been present in the isolated portion of the flow path from passing into the second fluid flow system component.

In further accordance with the present disclosure, a pre-assembled disposable medical fluid flow system may be provided comprising a first pre-sterilized fluid flow system component that includes a first fluid flow path segment and an openable closure isolating the first flow path segment from the remainder of the pre-sterilized fluid flow system component. The openable closure serves to maintain the sterility of the remainder of the first pre-sterilized fluid flow system component upon exposure of the first flow path segment to a non-sterile environment. The pre-assembled flow system also includes a second pre-sterilized fluid flow system component including a second fluid flow path segment and a micro-organism filter isolating the second flow path segment from the remainder of the second pre-sterilized fluid flow system component. The micro-organism filter serves to maintain the sterility of the remainder of the second pre-sterilized fluid flow system component upon exposure of the second flow path segment to a non-sterile environment. The first and second flow path segments are fixedly joined to provide fluid communication between the remainders of the first and second pre-sterilized fluid flow system component.

Such a system may be made, for example, by sterilizing a first fluid flow system component that includes a first fluid flow path segment and isolating the first flow path segment from the remainder of the first pre-sterilized fluid flow system component by an openable closure to maintain sterility of the remainder of the first fluid flow system component. A second fluid flow system component including a second fluid flow path segment is also sterilized. The method includes isolating the second fluid flow path segment from the remainder of the second fluid flow system component by a micro-organism filter to maintain sterility of such remainder of the second pre-sterilized fluid flow system component. The first and second flow path segments are exposed to non-sterile environments, such as during the process of fixedly joining them to provide fluid communication between the remainders of the first and second fluid flow system components.

The resulting disposable medical fluid flow system has the advantages described earlier. It does not require the complicated electron beam sterilization or sterile docking procedures described in the prior art and yet is pre-attached or pre-assembled, so that the medical professional is not required to separately attach the first fluid flow system component to the second fluid flow system component. Nor is there the attendant administrative requirements or risks associated with separate ordering, inventorying or prescribing or assembling of the first and second fluid system components.

DESCRIPTION OF DRAWINGS

Turning now to a more detailed description of the present subject matter, which is shown for purposes of illustration and not limitation in the accompanying drawings, of which:

FIG. 2 is a plan view of one portion of the fluid flow system of FIG. 1.

FIG. 3 is a plan view of another embodiment of the subject matter of the present disclosure that may be employed in the fluid flow system illustrated for example in FIG. 1.

DETAILED DESCRIPTION

Figure 1:
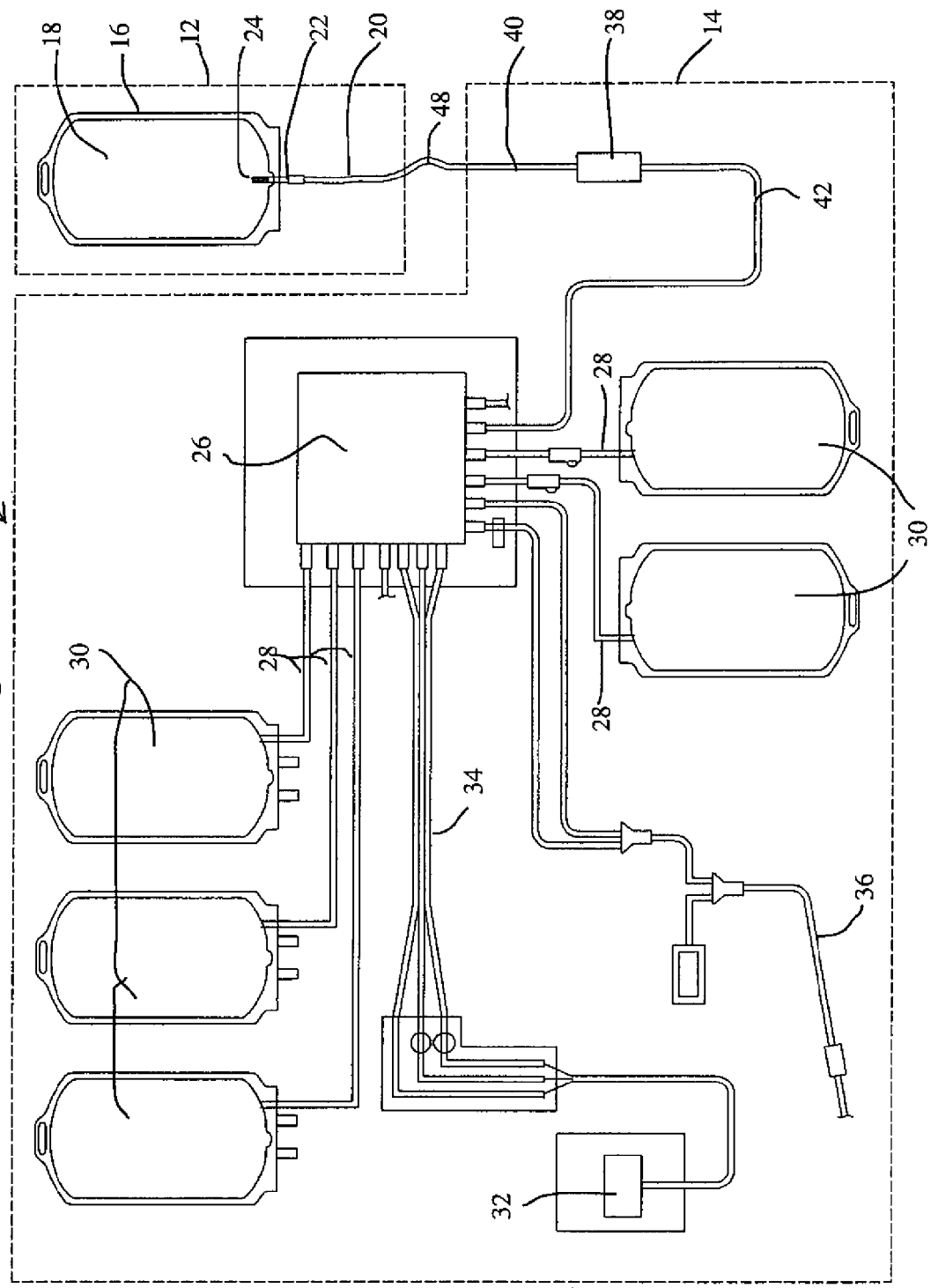
FIG. 1 is plan view of a pre-assembled disposable medical fluid flow system embodying the one aspect of the present subject matter.

FIG. 1 illustrates one form of a pre-assembled disposable medical fluid flow system 10 embodying one aspect of the present disclosure. For purposes of illustration, FIG. 1 depicts such a disposable medical fluid flow system of the type that may be associated with the ALYX Centrifugal Blood Processing System sold by Fenwal, Inc. of Lake Zurich, Ill., and illustrated in more detail, for example, in U.S. Pat. No. 6,322,488, which is hereby incorporated by reference. It should be understood that the ALYX disposable medical fluid flow system is employed in this application for purposes of illustration and not limitation. The present subject matter may be employed in a wide variety of disposable medical fluid flow systems, including without limitation, fluid flow systems (1) for administration of an agent for any diagnostic or therapeutic purpose, (2) for blood or blood component or other cellular collecting, storing or processing, (3) for use with systems or hardware such as supplied by Fenwal or its competitors, such as Gambro, Inc and Haemonetics Inc. and/or (4) for any other medical fluid flow system application where sterile collecting, storing or processing of fluid is desired, whether or not the system is directly attached to a human or animal.

More specifically, FIG. 1 illustrates a pre-assembled disposable medical flow system 10 which comprises at least two components and, more specifically, at least a first fluid system component 12 and a second fluid flow system component 14 which are illustrated generally within the rectangles formed by the dashed lines. It is within the scope of this description that the first and second components 12 and 14 may include any one or more parts or pieces of the overall system assembled in any desired way. Also, the components 12 and 14 may be part of a larger system, the other portions of which are assembled in a different manner than described herein and which are not necessarily pre-assembled in their entirety. Nor does this description preclude the possibility that other components are subsequently attached to or associated with components 12 and 14 or are added to the overall system in a manner different than described or claimed herein. Further, it should be understood that the system 10 may include a plurality of first and/or a plurality of second fluid flow system components interconnected as the particular system or application may require.

As shown for purposes of illustration, the first fluid flow system component 12 includes a container 16 of medical agent 18, such as liquid saline, anticoagulant or cell preservative, although any desired liquid, drug or other agent is within the scope of disclosure. As illustrated, the container is intended to represent a common flexible plastic medical fluid container of material, such as PVC, EVA or other material, compatible with the agent contained therein.

For accessing the contents of the container 16 and communicating with the second fluid flow system component 14, a length of tubing 20 is pre-attached to a port 22 of the container 16, and forms a first segment of a flow path between the first and second fluid flow system components. In the illustrated embodiment, the inside of the container 16 and its contents 18 are isolated from the tubing 20, and flow is prevented, by an openable closure 24, which is normally closed to contain the contents within the container and to prevent bacteria or other microorganisms from contaminating the agent 18.

The openable closure may be located at various different positions, such as in the port 22 or along the tubing 20. Preferably the openable closure can be opened by the user, for example, by manual manipulation. The openable closure may take any of a variety of forms, such as clamp (not shown), for example a slide clamp or roller clamp or other type of clamp which can reliably isolate the contents of the container 16. As illustrated, the openable closure is in the form of a frangible member which normally blocks fluid flow through port 22 but may be broken and opened by manual manipulation through the flexible walls of container 16. Such frangible closures are well known in the medical device field, and examples are depicted in U.S. Pat. Nos. 4,181,140 and 4,294,247, which are incorporated by reference herein. Whether the openable closure is a clamp, frangible closure or other type of closure, it serves to isolate the contents of the container from all or least a portion of the downstream tubing 20 to maintain the sterility of the contents as will be described more fully below.

Because the agent 18 in the container 16 is sealed from the atmosphere, sterilization can only be carried out in certain ways. For example, the use of gas sterilization, such as by exposure to ethylene oxide, would be ineffective for the contents of the sealed container 16. In addition, radiation sterilization, even if theoretically feasible for sterilizing the contents of the container, may not be viewed as suitable because of potential deleterious effects on the agent 18. One of the most common ways to sterilize containers of medical fluid is autoclave or steam sterilization, but steam sterilization may not be as efficient or reliable for other portions of the fluid flow system or may not be desired for other reasons. In theory, the container 16 also could have been pre-filled with the agent 18 in a sterile filling process, and separate sterilization of the filled container not required. In that event, however, it may be preferred that the container 16 and contents 18 not be attached to other parts of the fluid flow system during sterilization of those other parts to avoid any potential adverse effect on the contents 18 or for other reasons of cost or efficiency. Therefore, for a variety of reasons it may be necessary or preferred to manufacture and/or sterilize the first component 12, including the container 16 and agent 18, separately from other portions of the fluid flow system.

The second fluid flow system component 14, as shown in FIG. 1, is intended to illustrate one or more portions of a medical fluid flow system that does not contain any substantial liquids or other agents for which different sterilization techniques are preferred or necessary, or which is provided separately from the first component 12 for other reasons, such as manufacturing efficiency. The particular second flow system component illustrated in FIG. 1 includes, for example, a rigid plastic fluid flow control cassette 26, fluid flow tubing 28 connecting the cassette to one or more empty containers 30, a centrifugal processing chamber 32, an umbilicus flow path arrangement 34 for communicating with the centrifuge chamber, and access tubing 36, which may include one or more needles or other access devices, for accessing the vascular system of a patient or donor.

Although the various elements of the second component 14 are structurally quite different, what they have in common is that individually and together, as illustrated, they are suitable for sterilization by means that is inconsistent with or not preferred for sterilizing the first flow system component 12. As shown for purposes of illustration and not limitation, the second fluid flow system component 14 contains no substantial amounts of liquids, drugs or other agents that would potentially limit the type of sterilization that may otherwise be appropriate for such a system. As such, the second component 14 may be sterilized by radiation sterilization or by exposure to sterilizing gas such as ethylene oxide.

For fluid communication with the first fluid system component 12, the second component includes a length of tubing 40 forming a second segment of the flow path between the first and second components. The tubing 40 extends from the inlet port of a micro-organism filter porous filter 38 so that any fluid flowing from the first component through the tubing 20 must pass through the micro-organism filter before reaching the remainder of the second flow system component. The micro-organism filter may be of any suitable type, such as a membrane filter or depth filter or other type of filter, for blocking the passage of bacteria and preferably also viruses into the remainder of the second component 14 downstream of the filter.

More specifically, the filter 38 may comprise a rigid or flexible external housing having an inlet port, and outlet port and a filter media interposed therebetween. The filter media may be of any suitable construction, but a porous membrane having an effective pore size sufficiently small to block the passage of bacteria and also preferably viruses may be employed. Without limiting the possible filter media that may be used, one potential filter membrane may be a polymeric membrane such as those commercially available from Pall Corporation and others having an effective pore size of about 0.22 microns, which is sufficiently small to block both bacteria and viruses.

Making the Disposable Medical Fluid Flow System

In accordance with the present subject matter, the method for making the disposable medical fluid flow system of FIG. 1 does not require the complicated steps or procedures of the e-beam sterilization system or the sterile docking arrangement described above. Briefly stated, the first fluid system component 12, which, as illustrated, comprises a container 16 of medical liquid, a first fluid flow path segment in the form of tubing 20 and an openable closure, in the form of a frangible member 24, which isolates the contents of the container 16 from all or a distal portion of the tubing 20. The first blood component may be sterilized, for example, by heat sterilization in an autoclave or the like.

When removed from the autoclave, the tubing segment 20 may be exposed, by an open distal end to non-sterile atmosphere in the manufacturing facility. Thus, the sterile condition of the tubing 20 or a distal portion of the tubing cannot be assured, even though bacteria or viruses may not be present in any substantial numbers within the tubing due to inherent resistance of air inside the tubing to the transmission of bacteria or viruses. As suggested above, the use of the term "non-sterile" with reference to the flow path or any portion of the flow path or the disposable medical fluid flow system is not intended to imply or indicate that bacteria, viruses or other micro-organisms are actually present in the "non-sterile" portion. Instead, the term "non-sterile", is intended to include portions for which sterility cannot be assured, for example, by reason of exposure to the ambient atmosphere or other non-sterile environments that could potentially lead to the presence of bacteria, viruses or the like. Accordingly, unless otherwise stated, "non-sterile" is broadly intended to include situations where sterility cannot be assured, whether or not presence of bacteria or viruses is actually demonstrated.

Even though the tubing 20 is exposed to a non-sterile environment, the openable closure 24 in the form of a frangible cannula isolates the inside of the container 16 and preserves the sterility of the contents 18. Therefore, although the tubing downstream of the openable closure may be regarded as non-sterile because sterility cannot be assured, the sterility of the inside of the container 16 and agent 18 is preserved by the removable closure, which blocks communication between the inside of the container and the non-sterile portion of the tubing.

As shown for purposes of illustration, the second fluid flow system component 14 does not intentionally contain any substantial amounts of liquid. It can be sterilized, for example, by radiation sterilization or, depending on the various pieces or elements that make up the second component, by contact with sterilizing gas such as ethylene oxide. In any event, upon removal from the sterilizing process or atmosphere, the tubing 40 may be exposed via an open distal end to the non-sterile environment of the manufacturing facility. However, the micro-organism filter 38 isolates the remainder of the second fluid system component downstream of the filter to maintain the sterility of the remainder of the system, despite the fact that the tubing segment 40 is exposed to non-sterile atmosphere and thus its sterility cannot be assured. As indicated above, for purposes of the present description, references to "non-sterile" include situations involving both actual presence of bacteria and/or viruses and situations where although bacteria and/or virus may not be present, but where sterility cannot be assured.

Following separate sterilization of the first and second components of the fluid flow system, tubing segments 20 and 40 are sealed together fixedly at a line or area of joinder 48 to form a single integral pre-assembled disposable medical fluid system 10 that comprises at least the first and second fluid flow system components. Any suitable method for joining the flow the tubing segments may be employed including mechanical couplings, solvent bonding directly or with an intermediate coupling, heat seals or other suitable couplings, provided that the tubings are fixedly joined together to provide an integral assembled system prior to shipment to the end user, and fluid communication between tubing segment 20 and 40 is provided.

Method of Use

When the medical fluid flow system 10 is provided to the ultimate user, it is provided as a single pre-assembled or integral disposable medical fluid flow system. That does not, however, preclude the attachment of additional flow components as may be required for the end use of the particular system. In other words, the fact that the first and second flow system components are sterilized and assembled in the manner described herein does not preclude the addition of other elements features or components to the flow system 10 either by open attachment or sterile docking or other means as described in the prior art, either at the time of manufacture or later.

When the user is ready to use the system 10 employing the first and second fluid system components, the user will open the closure member 24, preferably manually such as by breaking a frangible cannula or opening a clamp, allowing medical fluid to flow from the container 16 into the tubing 20 forming a first segment of the flow path to the second flow system component. From tubing 20, the fluid passes into the tubing 40 of the second component and into and through the micro-organism filter 38. In the event that micro-organisms such as bacteria are present in the tubing 20 and/or 40, such as by exposure to non-sterile ambient atmosphere in the manufacturing facility, any such bacteria, and preferably any viruses, will be removed by the micro-organism filter 38 before the liquid passes into the remainder of the second fluid flow system component.

With this arrangement, the end user is not required to maintain separate inventories of the first and second fluid system components, is not required to separately order or prescribe the components, and is not required to assemble the first and second fluid system components, unlike the prior art systems, described above.

Other Figures

FIG. 2 shows the first fluid system component 12 and a portion of the second fluid system component 14 in an enlarged and isolated view. As seen there, the first component comprises at least one container 16 having a medical agent 18 contained therein. The tubing 20 forms a first flow path segment and is attached to a port 22 on the container for accessing the container contents. The container contents are isolated from the tubing by an openable closure 24 which in the illustrated FIG. 2 comprises a frangible member which may be broken and opened by manual manipulation through the flexible walls of the container 16. The tubing segment 20 terminates in a free end, which may be open to the ambient atmosphere or may be sealed, for joining to the second fluid system component 14.

The second fluid system component 14 is partially shown and comprises tubing 40 forming a second flow path segment leading to the micro-organism filter 38. Tubing 42 extends from the micro-organism filter 38 to the remainder of the second fluid flow system component. As noted above, the second fluid flow system component may be a relatively simple length of tubing with any required flow control devices or patient/donor access needles or access devices or may be a more complex system including a variety of components as illustrated for example in FIG. 1, where the second fluid system component includes flow control cassette, multiple empty containers, blood processing chambers and the like.

As noted above, the first fluid system component is preferably separately sterilized from the second fluid flow system component or otherwise separately provided, and after removal from the sterilizer, the tubing 20 it may be exposed, via an open end, to non-sterile ambient environment of the manufacturing facility. Notwithstanding that, the frangible member 24 isolates sterile contents 18 of container 16 from the inside of tubing 20.

Similarly, the second fluid flow system component is sterilized, for example by a sterilization technique different from that employed in connection with the first component, such as radiation or ethylene oxide sterilization. The second blood component includes a second fluid flow path segment defined by the tubing 40 which extends from the micro-organism filter 38. When the second flow system component is removed from the sterilization procedure, the tubing 40 may be exposed, by way of an open end to the non-sterile ambient environment of the manufacturing work place. Notwithstanding that, the micro-organism filter prevents the passage of at least bacteria, and preferably both bacteria and viruses, into the remainder of the second fluid system component.

Thereafter, the tubing 20 and tubing 40 are joined together in a fixed integral connection to provide for fluid flow between the pre-sterilized remainder of the first fluid flow system upstream of the openable closure 24 (e.g., the container 16 and sterile contents 18) and the pre-sterilized remainder of the second fluid flow system component downstream of the micro-organism filter 38 (e.g., the cassette 28, empty containers 30, processing chamber 32, etc.). Even though micro-organisms may not be present or may not be present in significant numbers, sterility of the tubing 20 and tubing 40 is not assured due to ambient air exposure, and for purposes of this description, is referred to as non-sterile. Accordingly, the tubings 20 and 40 form a non-sterile flow path segment or length of tubing 44 between the remainder of the first fluid flow system component and the remainder of the second fluid flow system component or, in other words, between the openable closure 24 and the micro-organism filter 38. The openable closure 24, such as the frangible cannula, isolates the sterile contents of the container 16 from the non-sterile portion 44 of the flow path extending between the container 16 and the micro-organism filter 38. Similarly, the micro-organism filter 38 isolates the remainder of the second fluid flow system component from the non-sterile portion 44 of the flow path.

As described above, when fluid access is desired, the frangible 24 may be manually broken, allowing the contents 18 to flow through the non-sterile portion 44 of tubing 20 and 40 and through the micro-organism filter into the remainder of the second fluid flow system component. Because all of the fluid flowing from the container 16 must flow through the micro-organism filter 38 before reaching the remainder of the second fluid system component, any bacteria that is present in the non-sterile segment 44 of the flow path is removed by the micro-organism filter 38.

Although FIGS. 1 and 2 illustrate a medical fluid flow system having only one container 16 of medical fluid 18, it is within the scope of this disclosure for the pre-assembled disposable medical fluid flow system to have multiple sterilized fluid flow system components, each of which include one or more containers of sterile medical fluid. Similarly it is within the scope of the present disclosure that there be a plurality of second sterilized fluid system components that are separately sterilized and may be in fluid communication with one or more or all of multiple first fluid system components, depending on the particular application or usage of the disposable medical fluid flow system.

FIG. 3 illustrates an embodiment similar to that shown in FIG. 2 with the exception that the embodiment FIG. 3 includes an additional openable closure member 46 located between the micro-organism filter 38 and the openable closure 24. In this embodiment, the non-sterile portion 44 of the flow path formed by distal portions of the tubing 20 and 40 is located between the openable closures 46 and 24. Further in this embodiment, both openable closures are illustrated in the form of frangible members that normally block fluid flow from the container 16 or through the tubing 40 but may be opened by manual manipulation of the user. Again, consistent with the subject matter disclosed herein, the final pre-assembled disposable medical fluid flow system 10 may comprise one or more first sterilized fluid system components 12 and one or more second sterilized fluid flow system components 14 that are all in fluid flow communication or are in fluid flow communication with selected other components, as the particular design of the disposable fluid flow system may dictate.

In any event, as a consequence of the subject matter disclosed herein, a pre-assembled medical fluid flow system may be provided which does not require separate inventorying, ordering, prescribing or assembling by the user, while preserving the advantages of a completely sterilized fluid flow system. Although described in terms of the illustrated and preferred embodiments, it is understood that the present subject matter may be employed in other configurations and include other features, components and systems as the particular application may require and may be apparent upon review of this description.

The invention claimed is:

1. A pre-assembled disposable medical fluid flow system comprising:
   a first sterilized fluid flow system component;
   a second sterilized fluid flow system component;
   a flow path fixedly connected to the first and second sterilized fluid flow system components for providing fluid communication therebetween, the flow path including an isolated portion between the first and second sterilized fluid flow system components;
   wherein the isolated portion of the flow path is non-sterile and includes a connection region;

an openable closure isolating the first sterilized fluid system component from the isolated portion of the flow path; and a micro-organism filter disposed between and isolating the isolated portion of the flow path and the second sterilized fluid flow system component such that any fluid from the isolated portion of the flow path must flow through the micro-organism filter to reach the second sterilized fluid flow system component.

2. The pre-assembled disposable medical fluid flow system of claim 1 in which the first sterilized fluid flow system component comprises a sterile agent for administration to a patient.

3. The pre-assembled disposable medical fluid flow system of claim 2 in which the first sterilized fluid flow system component comprises a liquid.

4. The pre-assembled disposable medical fluid flow system of claim 1 in which the second sterilized fluid system component is suited for sterilization by one or more sterilization techniques, and the first fluid sterilized system component is not suited for sterilization by such one or more selected techniques.

5. The pre-assembled disposable medical fluid flow system of claim 1 in which the first sterilized fluid system component comprises a container of sterile liquid and the second sterilized fluid system does not contain any substantial quantity of liquid.

6. The pre-assembled disposable medical fluid flow system of claim 1 in which the openable closure comprises a clamp or a frangible member.

7. The pre-assembled disposable medical fluid flow system of claim 1 in which the micro-organism filter comprises a filter media having an effective pore size sufficient to block bacteria and viruses.

8. The pre-assembled disposable medical fluid flow system of claim 7 in which the filter media has an effective pore size less than about 0.22 microns.

9. The pre-assembled disposable medical fluid flow system of claim 1 further comprising a second openable closure isolating the micro-organism filter from the isolated portion of the flow path.

10. The pre-assembled disposable medical fluid flow system of claim 1 wherein the connection region includes at least one solvent bond.

11. A method for making a disposable medical fluid flow system comprising:

sterilizing a first fluid flow system component;

sterilizing a second fluid flow system component;

providing a fluid flow path between the first and second sterilized fluid flow system components and fixedly attached thereto to provide a preassembled fluid flow system, the fluid flow path of such preassembled system including an isolated portion between the first and second sterilized fluid flow system components;

providing an openable closure for isolating the first sterilized fluid flow system component from the isolated portion of the flow path; and the isolated portion including a non-sterile zone including a connection region; and providing a micro-organism filter between the portion of the flow path and the second sterilized fluid flow system component to isolate the portion of the flow path and filter any fluid passing from the isolated portion of the flow path to the second sterilized fluid flow system component.

12. The method of claim 11 in which the first fluid flow system component comprises an agent for administration to a patient.

13. The method of claim 11 in which the first fluid flow system component comprises a liquid.

14. The method of claim 11 in which the second fluid system component is sterilized by a method different than the first fluid system component.

15. The method of claim 11 in which the first fluid system component comprises a container of sterile liquid and the second fluid system does not contain any substantial quantity of liquid.

16. The method of claim 11 in which the openable closure comprises a clamp or a frangible member.

17. The method of claim 11 in which the micro-organism filter comprises a filter media having an effective pore size sufficient to filter out bacteria and viruses.

18. The method of claim 17 in which the filter media has an effective pore size less than about 0.22 microns.

19. The method of claim 11 wherein the connection region includes at least one solvent bond.

* * * * *